United States Patent
House et al.

(10) Patent No.: US 6,656,885 B2
(45) Date of Patent: Dec. 2, 2003

(54) ANHYDRIDE-MODIFIED CHITOSAN, METHOD OF PREPARATION THEREOF, AND FLUIDS CONTAINING SAME

(75) Inventors: Roy F. House, Houston, TX (US); Diane M. Smith, Donaldsonville, LA (US)

(73) Assignee: Venture Innovations, Inc., Lafayette, LA (US)

( * ) Notice: Subject to any disclaimer, the term of this patent is extended or adjusted under 35 U.S.C. 154(b) by 37 days.

(21) Appl. No.: 10/035,262

(22) Filed: Jan. 3, 2002

(65) Prior Publication Data

US 2002/0098987 A1 Jul. 25, 2002

Related U.S. Application Data

(63) Continuation-in-part of application No. 09/782,633, filed on Feb. 13, 2001, now Pat. No. 6,358,889, which is a continuation-in-part of application No. 09/222,293, filed on Dec. 28, 1998, now Pat. No. 6,258,755.

(51) Int. Cl.$^7$ .............................. C09K 7/02; C08B 37/08
(52) U.S. Cl. ....................... 507/110; 507/209; 507/211; 536/20; 536/55.3
(58) Field of Search ................. 507/110, 209, 507/211; 536/20, 55.3

(56) References Cited

U.S. PATENT DOCUMENTS

| | | | | | |
|---|---|---|---|---|---|
| 3,953,608 | A | * | 4/1976 | Vanlerberghe | 536/20 |
| 4,996,307 | A | * | 2/1991 | Itoi et al. | 536/20 |
| 5,077,052 | A | * | 12/1991 | Franzoni et al. | 536/20 |
| 5,874,551 | A | * | 2/1999 | Glasser et al. | 536/20 |
| 6,509,039 | B1 | * | 1/2003 | Nies | 536/20 |

* cited by examiner

*Primary Examiner*—Philip Tucker
(74) *Attorney, Agent, or Firm*—Roy F. House

(57) ABSTRACT

The invention provides an organic diacid anhydride-modified chitosan containing a polar additive comprising water soluble compounds containing one or more hydroxyl groups or one or more amino groups, including compounds containing both hydroxyl and amine groups, having a molecular weight less than about 2000, preferably less than about 1000. The invention also provides fluids useful in various well drilling and servicing operations comprising an alkaline aqueous liquid containing an organic diacid anhydride, chitosan, and the polar additive therein, as well as a method of drilling wells therewith.

39 Claims, No Drawings

ANHYDRIDE-MODIFIED CHITOSAN, METHOD OF PREPARATION THEREOF, AND FLUIDS CONTAINING SAME

The present patent application is a continuation-in-part application of patent application Ser. No. 09/782,633 filed Feb. 13, 2001 now U.S. Pat. No. 6,358,889, incorporated herein by reference, which is a continuation-in-part application of patent application Ser. No. 09/222,293 filed Dec. 28, 1998, now U.S. Pat. No. 6,258,755.

This invention was made with Government support under Award No. DMI-9901868 awarded by the National Science Foundation. The Government has certain rights in this invention.

FIELD OF THE INVENTION

The invention pertains to the modification of chitosan to produce viscosifiers (thickeners) for aqueous liquids, and to viscosified aqueous fluids containing such modified chitosans dispersed therein, and to methods of drilling a well utilizing such fluids.

BACKGROUND OF THE INVENTION

Many viscosifiers for, and methods of, increasing the viscosity of aqueous liquids are known. Such viscosifiers may be so-called water-soluble polymers such as biopolymers, gums, cellulose derivatives, alginates, and other polysaccharides or polysaccharide derivatives, and various synthetic polymers. Representative polymers are set forth in the book "Handbook of Water Soluble Gums and Resins," Robert L. Davidson, Ed., 1980.

Viscoelastic fluids are characterized as having a Theological profile which is shear thinning, having a high viscosity at extremely low shear rates and a low viscosity at high shear rates. Thus such fluids are pseudoplastic having a high yield stress.

This type of rheology is produced by hydrating in the fluid certain water soluble polymers or other colloidal materials. These polymers presently known are biopolymers, i.e., microbially produced polysaccharides or heteropolysaccharides, and are well known in the art.

There is a need for fluids which exhibit a high low shear rate viscosity which are shear thinning.

Chitosan is a partially or fully deacetylated form of chitin, a naturally occurring polysaccharide. Structurally, chitin is a polysaccharide consisting of beta-(1→4)2-acetamido-2-deoxy-D-glucose units, some of which are deacetylated. The degree of deacetylation usually varies between 8 and 15 percent, but depends on the species from which the chitin is obtained, and the method used for isolation and purification.

Chitin is not one polymer with a fixed stoichiometry, but a class of polymers of N-acetylglucosamine with different crystal structures and degrees of deacetylation, and with fairly large variability from species to species. The polysaccharide obtained by more extensive deacetylation of chitin is chitosan.

Like chitin, chitosan is a generic term for a group of polymers of acetylglucosamine, but with a degree of deacetylation of between 50 and 100 percent. Chitosan is the beta-(1-4)-polysaccharide of D-glucosamine, and is structurally similar to cellulose, except that the C-2 hydroxyl group in cellulose is substituted with a primary amine group in chitosan. The large number of free amine groups (pKa= 6.3) makes chitosan a polymeric weak base. Both chitin and chitosan are insoluble in water, dilute aqueous bases, and most organic solvents. However, unlike chitin, chitosan is soluble in dilute aqueous acids, usually carboxylic acids, as the chitosonium salt. Solubility in dilute aqueous acid is therefore a simple way to distinguish chitin from chitosan.

Chitosan is unique in that it is a polysaccharide containing primary amine groups. Chitosan forms water-soluble salts with many organic and inorganic acids.

It is known to prepare chitosan derivatives by attaching various groups to one or more hydroxyl groups of the chitosan, as in various cellulose derivatives, and/or in attaching various groups to the primary amino group of chitosan.

U.S. Pat. Nos. 3,879,376 and 3,953,608 disclose chitosan derivatives formed by acylation of chitosan with a saturated or unsaturated organic diacid anhydride. The chitosan derivatives contain 5 to 30% acetylglucosamine, 5 to 40% glucosamine, and 30 to 90% of glucosamine units reacted with the diacid anhydride. The derivatives are prepared in an aqueous dispersion. They may be recovered by the addition of a solvent such as an alcohol to precipitate the derivative. The derivatives are useful in various cosmetic compositions.

U.S. Pat. No. 4,996,307 discloses the preparation of an acylated chitosan having a degree of acylation of 35 to 65% by dissolving a water-insoluble chitosan having a degree of deacetylation of at least 70% in an aqueous acid solution, diluting the solution with water or a water-soluble solvent and adding an acylation agent to the diluted solution. Preferred water miscible solvents are lower monohydric alcohols such as methanol, ethanol, isopropyl alcohol, butyl alcohol, etc., polyhydric alcohols such as glycerin, propylene glycol, etc. and ketones such as acetone. Disclosed acylation agents are anhydrides of monocarbocyclic acids having from 1 to 5 carbon atoms per acyl group and benzoic acid.

U.S. Pat. No. 5,061,792 discloses the preparation of chitosan salts by suspending the chitosan in about 5 to about 50 parts by weight of a $C_1$ to $C_3$ monohydric alcohol containing an amount of water sufficient to raise the dielectric constant of the alcohol to at least about 30 and not more than about 40, adding about 0.5 to about 4 equivalents for each equivalent of amino groups in the chitosan of an acid, maintaining the mixture until reaction between the chitosan and the acid is complete, and recovering and drying the chitosan salt. The concentrations of water in the alcohol solutions ranges as follows: methanol—0%–9.7% by weight; ethanol—4.4%–13.7% by weight; 1-propanol—5.8%–13.4% by weight; 2-propanol—6.7%–14.4% by weight.

U.S. Pat. No. 4,929,722 discloses the preparation of chitosan salts in a heterogenerous reaction between dissolved organic acids and chitosan dispersed in aqueous alcohols, inter alia, containing an amount of water in an amount up to about 65 wt. % of the total medium, preferably 30 to 45 wt. %, more preferably about 40 wt. %.

The following papers disclose the reaction of chitosan with various anhydrides: (1) "Formation and Characterization of a Physical Chitin Gel," L. Vachoud et al., Carbohydrate Research 302 (1977), 169–177; (2) "Chitosan Film Acylation and Effects on Biodegradability," Jin Xu et al., Macromolecules 1996, 29, 3436–3440; (3) "N-Acetylchitosan Gel: A Polyhydrate of Chitin," Shigehero Hirans et al., Biopolymers 15 (1976), 1685–1691.

SUMMARY OF THE INVENTION

We have now determined that aqueous alkaline fluids useful in oil and gas well operations, such as drilling, fracturing, sand control, lost circulation control, completion, workover and the like can be formulated to contain chitosan, an anhydride modifier, and a hydroxyl and/or amino-containing Polar Additive. The chitosan and anhydride react to increase the viscosity of the fluid. The Polar Additive increases the low shear rate viscosity and enhances the thermal stability of the fluids.

Thus, it is an object of the invention to provide aqueous alkaline well drilling and servicing fluids containing chitosan, an anhydride modifier, and a Polar Additive.

It is another object of the invention to provide an organic diacid anhydride-modified chitosan containing a Polar Additive as subsequently disclosed hereinafter.

Another object of the invention is to provide a method of drilling a well comprising circulating in a wellbore during drilling an aqueous alkaline fluid containing chitosan, an anhydride modifier therefore, and a Polar Additive as subsequently disclosed hereinafter.

Still another object of the invention is to provide a method of preparing an organic diacid anhydride-modified chitosan containing a Polar Additive as subsequently disclosed hereinafter.

These and other objects of this invention will be apparent to one skilled in the art upon reading this specification and the appended claims.

While the invention is susceptible of various modifications and alternative forms, specific embodiments thereof will hereinafter be described in detail and shown by way of example. It should be understood, however, that it is not intended to limit the invention to the particular forms disclosed, but, on the contrary, the invention is to cover all modifications and alternatives falling within the spirit and scope of the invention as expressed in the appended claims.

The compositions can comprise, consist essentially of, or consist of the stated materials. The method can comprise, consist essentially of, or consist of the stated steps with the stated materials.

DETAILED DESCRIPTION AND PREFERRED EMBODIMENTS

The invention provides oil and gas well drilling and servicing fluids containing chitosan which is modified with one or more organic diacid anhydrides and one or more Polar Additives as hereinafter disclosed. The fluids are useful in various operations such as drilling, fracturing, sand control, lost circulation control, completion, workover, and the like. The preferred fluids are alkaline aqueous pseudoplastic fluids having a Brookfield 0.3 rpm viscosity (hereinafter sometimes referred to as "low shear rate viscosity" or "LSRV") of at least 10,000 centipoise and a shear thinning index (hereinafter sometimes referred to as "STI") greater than about 25. The STI is the ratio of the Brookfield viscosity at 0.3 rpm to the Brookfield viscosity at 100 rpm and is an indication of the shear thinning, pseudoplastic characteristic of the fluids. Preferably the LSRV is at least about 20,000 centipoise, most preferably at least about 30,000 centipoise.

The chitosans useful in the fluids will have at least 50% of their amino groups deacetylated, i.e., the degree of deacetylation is at least 50%, preferably at least 70%, and most preferably from about 85% to 100%.

The concentration of chitosan in the fluids will be sufficient, when reacted with the anhydride(s) and Polar Additive, to impart to the fluids the rheological characteristics desired. Generally the concentration of chitosan will be from about 0.5 lb/bbl (0.143% w/v) to about 6 lb/bbl (1.715% w/v), preferably from about 2 lb/bbl (0.572% w/v) to about 5 lb/bbl (1.429 % w/v).

The concentration of the Polar Additive in the fluids should be sufficient to increase the LSRV of the fluids, after aging the fluids at 180° F. (82.2° C.), as compared to the LSRV of the fluids before aging. Generally the fluids will contain from about 0.5 ppb to about 25 ppb of the Polar Additive, preferably from about 1 ppb to about 20 ppb, and most preferably from about 1 ppb to about 15 ppb.

The concentration of the anhydride in the fluids will be in amount to provide an anhydride to chitosan weight ratio from about 0.1 to 1 to about 1.5 to 1, preferably from about 0.2 to 1 to about 1 to 1.

The fluids are initially prepared by forming an aqueous chitosan solution/dispersion containing the anhydride modifier, and thereafter raising the pH to basic, i.e., to a pH of about 7.0 or above, preferably from about 8 to about 11. The Polar Additive can be added to the fluid either before or after raising the pH. Optionally, the anhydride modifier may be dissolved in the Polar Additive and added to the fluid.

The fluids may be prepared by forming an acidic aqueous chitosan solution/dispersion containing the anhydride modifier, wherein the pH is from about 2 to about 6, preferably from about 3 to about 5.5, and thereafter raising the pH to basic, i.e., to a pH of about 7.0 or above, preferably from about 8 to about 11. The Polar Additive can be added to the fluids either before or after raising the pH.

A wide variety of acids can be used to solublize chitosan. Such acids include inorganic acids such as hydrochloric acid, nitric acid, and sulfamic acid, and water soluble organic acids represented by the formula: R—(COOH)$_n$ wherein n has a value of 1 to 3 and R represents a mono- or divalent organic radical composed of carbon, hydrogen, and optionally at least one of oxygen, nitrogen, and sulfur. Exemplary organic acids are the mono- and dicarboxylic acids such as formic, acetic, N-acetylglycine, acetylsalicylic, glycolic, lactic, malic, 2-pyrrolidone-5-carboxylic, salicylic, glutamic, glutaric, malonic, and thioglycolic acids.

The preferred acid used to prepare the acidic chitosan solution is selected from the group consisting of (a) monocarboxylic acids containing from one to three carbon atoms, (b) substituted monocarboxylic acids containing at least one radical per molecule selected from the group consisting of hydroxyl, amino, chloro, and thio, and containing from one to three carbon atoms, and (c) mixtures thereof.

The concentration of acid should be sufficient to decrease the pH of the solution to less than about 6.0, preferably 5.5 or less.

The basic compound used to raise the pH to the alkaline range can be any compatible base which can be determined by routine testing. Preferred basic compounds are the alkali metal and ammonium hydroxides, carbonates and bisulfites, and mixtures thereof. Organic bases such as low molecular weight amines and hydroxyamines, such as ethanolamine and the like, can be used to raise the pH, also in combination with an inorganic basic compound. Preferred bases are the alkali metal carbonates.

The water base borehole fluids and well servicing fluids of this invention generally will contain materials well known in the art to provide various characteristics of properties to the fluid. Thus the fluids may contain one or more viscosifiers or suspending agents in addition to the chitosan, weighting agents, corrosion inhibitors, soluble salts, biocides, fungicides, seepage loss control additives, bridging agents, deflocculants, lubricity additives, shale control additives, pH control additives, and other additives as desired.

The borehole fluids may contain one or more materials which function as encapsulating or fluid loss control additives to restrict the entry of liquid from the fluid to the contacted shale. Representative materials known in the art include partially solublized starch, gelatinized starch, starch derivatives, cellulose derivatives, humic acid salts (lignite salts), lignosulfonates, gums, biopolymers, synthetic water soluble polymers, and mixtures thereof.

The oil and gas well drilling and servicing fluids of this invention preferably have a pH in the range from about 7.5 to about 11.5, most preferably from 8 to about 11.

If desired, water soluble potassium compounds can be incorporated into the fluids of this invention to increase the potassium ion content thereof Thus it is known to add potassium chloride, potassium formate, potassium acetate, and the like to fluids to enhance the shale stabilizing characteristics of the fluids.

The well drilling and servicing fluids of this invention contains an aqueous phase which may be fresh water, a natural brine, sea water or a formulated brine. The formulated brine is manufactured by dissolving one or more soluble salts in water, a natural brine, or sea water. Representative soluble salts are the chloride, bromide, acetate and formate salts of potassium, sodium, calcium, magnesium and zinc. The preferred salts contain a monovalent cation.

The borehole fluid of this invention is circulated or spotted within a borehole during well drilling or servicing operations as is well known in the art. Fracturing fluids are used to hydraulically fracture subterranean formations as is well known in the art.

The fluids of the invention can also optionally contain one or more aldehydes to react with the chitosan and the acylated chitosan derivatives present in the fluids. Generally the concentration of the aldehyde will be from about 0.7 kg/m$^3$ (0.25 ppb) to about 57 kg/m$^3$ (20 ppb), preferably from about 0.7 kg/r$^3$ (0.25 ppb) to about 43 kg/m$^3$ (15 ppb).

It is one aspect of this invention to provide an anhydride-modified chitosan containing the Polar Additive (hereinafter sometimes referred to as AMCCPA). The AMCCPA is prepared in a heterogeneous process by mixing together the chitosan, anhydride, polar additive, and water under high shear. The relative concentrations of the chitosan, anhydride, Polar Additive, and water in the AMCCPA are such as to provide the desired concentrations of the chitosan, anhydride, and Polar Additive in the fluids containing the AMCCPA. Generally the relative concentrations are as follows: chitosan=20% to 60% by weight; anhydride=5% to 45% by weight; Polar Additive=10% to 25% by weight; and water=10% to 30% by weight.

Exemplary mixers include the Littleford Day Double Arm Mixers, Littleford FKM and KM Mixers, with or without choppers, Littleford POLYPHASE® Mixers, Ross Double Planetary Mixer, Baker Perkins Twin-Screw Continuous Mixers, Processall Mixmill, mixer-extruders, and the like.

The addition of the chitosan, anhydride, Polar Additive, and water can be added to the mixer in any order. Thus the water can be added to the chitosan to hydrate it, followed by addition of the anhydride and the Polar Additive. Alternatively, the Polar Additive can be mixed with the anhydride to solublize it, optionally also with the water, before addition to the chitosan.

The AMCCPA is generally a powder which is preferably ground before use. Preferably the particle size of the AMCCPA is less than 60 mesh, U.S. Standard Sieve Series.

If desired, the concentration of water and/or Polar Additive can be increased, while maintaining the desired anhydride to chitosan weight ratio to produce a liquid anhydride-modified chitosan concentrate suitable to be added to an aqueous liquid to produce the fluids of the invention. Alternatively, the AMCCPA can be suspended in a liquid other than water and/or the Polar Additive to produce a AMCCPA suspension suitable for addition to an aqueous liquid to increase the viscosity thereof.

The anhydride modifiers suitable for use in the present invention are saturated or unsaturated organic diacid anhydrides, substituted products of such anhydrides, and mixtures thereof, wherein the substituted products contain one or more functional groups selected from the group consisting of hydroxyl, carboxyl, alkenyl, amino, and mixtures thereof. Exemplary saturated anhydrides are succinic anhydride (preferred), acetoxysuccinic anhydride, methylsuccinic anhydride, diacetyl tartaric anhydride, tartaric anhydride, glutaric anhydride, glutamic anhydride, and the like. Exemplary unsaturated anhydrides used can be maleic anhydride (preferred), itaconic anhydride, citraconic anhydride, dodecenylsuccinic anhydrides, octadecenylsuccinic anhydride, other alkenyl succinic anhydrides, and the like wherein the alkenyl group contains from about 2 to about 20 carbon atoms, and mixtures thereof.

The concentration of the organic diacid anhydride in the fluid is from about 10% to about 250% of the weight of chitosan in the fluid, i.e., the weight ratio of anhydride to chitosan is from about 0.1 to 1 to about 2.5 to 1. It is preferred that the weight ratio of the succinic anhydride to chitosan is from about 0.1 to 1 to about 1.5 to 1.

Alkanoic acid anhydrides (alkanoic anhydrides) such as acetic anhydride, propionic anhydride, butyric anhydride, dodecanoic anhydride, and the like can be used together with the organic diacid anhydrides, if desired.

The Polar Additives suitable for use in the present invention are water soluble compounds containing one or more hydroxyl groups, or one or more amino groups, including compounds containing both hydroxyl and amino groups, having a molecular weight less than about 2000, preferably less than about 1000.

Exemplary hydroxyl-containing compounds include: monoalcohols containing from one to about six carbon atoms; polyalcohols such as those disclosed in Hale et al. U.S. Pat. No. 5,436,227, incorporated herein by reference, and in Hale et al. U.S. Pat. No. 5,058,679, incorporated herein by reference; and glycol ethers having the empirical formula H—[(OC$_2$H$_4$)$_a$(OC$_3$H$_4$)$_b$]—OR where R contains from one to about eight carbon atoms, and where a and b independently are zero, with the proviso that a≠b, or integers such that the average molecular weight of the glycol ether is less than about 2000, preferably less than about 1000. Exemplary polyalcohols include polyols having at least two carbon atoms and two hydroxyl groups but no more than 18 carbon atoms and 31 hydroxyl groups. Non-limitive examples of such polyalcohols include (carbon chains may be straight chains, breached chains, aromatic, or alicyclic), ethylene glycol, diethylene glycol, 1,2-propranadiol, 1-3-propanadiol (propylene glycol), neopentyl glycol, pentaerythritol, 1,6-hexanediol; glycerol, open and cyclic condensation products of glycerol (and/or other polyalcohols) such as diglycerols, triglycerols, tetraglycerols, pentaglycerols, and hexaglycerols; polyalkyleneglycols such as polyethyleneglycols, polypropyleneglycols, ethylenepropyleneglycol, polyethylenepropylene glycols, ethylenepropylene glycol copolymers, and ethylenebutylene glycol copolymers and 1,5,6,9-decanetetrol, 1,1,4,4-cyclohexanetetramethanol, 1,2, 4,5-cyclohexanetetramethanol, 1,4-cyclohexanedimethanol, 1,3-cyclopentanedimethanol, 1,2,4,7-hepanetetrol, 1,2,3,5-heptanetetrol, 1,5,8-nonanetriol, 1,5,9-nonanetriol, 1,3,5,9-heptanetetrol, 1,3,5-heptanetriol, 2,4,6-heptanetriol, 4,4-dimethyl-1,2,3-pentanetriol, 1,1,3-cyclohexanetrimethanol, 1,3,4-cycloheptanetriol, 1,1-cyclopropanediol, 1,2-cyclopropanediol, 1,2,3-cyclopropanetriol, 1,1-cyclopropanedimethanol, 1,2-cyclopropanedimethanol, 1,2,3-cyclopropanetrimethanol, 1,1-cyclobutanediol, 1,2-cyclobutanediol, 1,3-cyclobutanediol, 1,2-cyclobutane dimethanol, 1,2,3-cyclobutanetriol, 1,2,4-cyclobutanetriol, 1,2,3,4-cyclobutanetetrol, 1,3-dimethyl-1,2,3,4-cyclobutanetetrol 1-hydroxcyclobutane methanol, 2-methyl-1-2-butanediol, 2-methyl-1,2-butanediol, 3-methyl-2,2-butanediol, 1,2-pentanediol, 1-3-pentanediol, 1,4-pentanediol, 2,3-pentanediol, 2,4-pentanediol, 1,2,3-pentanetriol, 1,2,4-pentanetriol, 2,3,4-pentanetriol, 1,1-cyclopentanediol, 1,2-cyclopentanediol, 1,3-cyclopentanediol, 1,2,3-cyclopentanetriol, 1,2-hexanediol, 1,3-hexanediol, 1,2,3-hexanetriol, 1,2,4-hexanetriol, 1,2,3,4-hexanetetrol, 1,1-cyclohexanediol, 1,2-cyclohexanediol, 1,4-cyclonexanediol, 1,2,4-cyclohexanetriol, 1,2,5-cyclohexanetriol, 1,2,3,4-cyclohexanetetrol, 1,2,3,5-cyclohexanetetrol, and mixtures thereof.

Exemplary amino-containing compounds include: monoamines containing from one to about six carbon atoms; and polyamines such as (1) polyethylenepolyamines containing up to about twenty carbon atoms, (2) alkylated polyamines having the empirical formula $R'$—[(NH—$C_2H_4)_c$ (NH—$C_3H_6)_d$—$NH_2$ where $R'$ contains from one to about 8 carbon atoms, and where c and d are integers such that the average molecular weight of the alkylated polyamine is less than about 2000, preferably less than about 1000, (3) amine-terminated ethoxylated glycols having the empirical formula $NH_2$—$(C_2H_4O)_e$—$C_2H_4$ $NH_2$ where e is an integer from 1 to about 20, and (4) amine-terminated ethoxylated amines having the empirical formula $A_2$—N—$(C_2H4NA)_fA$ where A is independently selected from the group consisting of H and $H_2N$—$(C_2H_4O)_g$ where each g is an integer from 1 to about 10, and wherein f is an integer from zero to a value wherein the total number of ethoxy-groups ($C_2H_4O$) is such that the molecular weight is less than about 2000, preferably less than about 1000.

Exemplary hydroxyl and amino-containing compounds include: amino-substituted aliphatic alcohols having the empirical formula Z—$(CZH_g)_h$—Z where each Z is independently selected from the group consisting of N≡, $NH_2$, OH, and H, provided that at least one Z is OH and at least one Z is $NH_2$, and where g is 0 or 1 with the proviso that when g is 0, Z is N≡, and h is an integer such that the molecular weight is less than about 2000, preferably less than about 1000; and ethoxylated amines having the empirical formula $D_2N$—$[(C_2H_4ND)_kD$ where each D is independently selected from the group consisting of H and HO—$(C_2H_4O)_m$, where m is an integer from 1 to about 10, and where k is an integer from 0 to a value wherein the total number of ethoxy groups ($C_2H_4O$) is such that the molecular weight is less than about 2000.

As indicated hereinbefore, the fluids set forth herein are useful in drilling a well in a rotary drilling process wherein there is circulated in a wellbore (borehole) a drilling fluid during the drilling thereof. Such processes are well known in the art. Generally, the method of drilling a well penetrating a subterranean formation comprises circulating an aqueous alkaline chitosan and anhydride-containing fluid as set forth herein through the well by introducing the drilling fluid into the well and into contact with the formation and withdrawing the drilling fluid from the well to remove cuttings therefrom. The fluids can be formulated for use as spotting fluids for use in releasing stuck pipe or tools within a borehole wherein the fluid is circulated to the depth in the borehole of the stuck pipe or tool and in a volume sufficient to displace the fluid in the borehole over the entire stuck area, and allowing the spotting fluid to soak for a period of time sufficient to release the stuck pipe or tool. The fluids can be formulated to provide viscous gels to overcome lost circulation problems in a wellbore as is known in the art.

In order to more completely describe the invention, the following non-limiting examples are given. In these examples and in this specification, the following abbreviations may be used: ml=milliliter; cp=centipoise; ppb=pounds per 42 gallon barrel; ND=not determined; PV=API plastic viscosity in centipoise; YP=API yield point in pounds per 100 square feet; rpm=revolutions per minute; API=American Petroleum Institute; LSRV=low shear rate viscosity in centipoise as determined with a Brookfield Viscometer at 0.3 rpm; STI=the shear thinning index obtained with a Brookfield Viscometer, which is the ratio of the 0.3 rpm viscosity to the 100 rpm viscosity; lb/100=$ft^2$=pounds per 100 square feet; $km^3$=kilograms per cubic meter.

EXAMPLES 1–26

Succinic Anhydride Modified Chitosan (SAMC) Preparation Procedure

Spray 15 parts by weight (pbw) of chitosan with the indicated initial pbw water. Place in a 12 speed Osterizer blendor jar. Add 7.5 pbw succinic anhydride and mix for 30 minutes on low (grate). Stop the blendor every 3 minutes to remove the powder from the sides of the blendor to ensure complete mixing. Cool to ambient temperature. Add the indicated concentration of additional water or methanol or Other Modifier and mix for an additional 15–30 minutes, as before. The composition of the SAMC samples is set forth in Table 1.

SAMC Sample Evaluation Procedure

In a 12 speed Osterizer blendor jar add 5 grams of soda ash to 350 ml of water. Add the indicated concentration of SAMC and shear on low (grate) for 3 minutes. Add the indicated concentration of methanol and shear for an additional 90 seconds. Add the indicated concentration of aphron-generating BLUE STREAK™ surfactant (product of MASI, LLC., Houston, Tex.) and shear for one additional minute. Determine the initial properties set forth in tables 2–6, allowing the fluids to set for 2 hours before the rheologies are obtained. Hot roll the fluids at 180F. for 16 hours. Cool the fluids and re-shear the fluids for 2 minutes. Determine the properties set forth in tables 2–6.

EXAMPLES 27–38

Several Polar Additives were evaluated in the alkaline anhydride-modified chitosan containing fluids by mixing on the 12 speed Osterizer blendor 5 grams of soda ash, 350 ml of water, 8.6 grams of SAMC #1, and 10 grams of each Polar Additive set forth in Tables 7 and 8 on low shear for 3 minutes. The fluids were evaluated for pH and the rheological properties set forth in Table 8.

EXAMPLE 39

Oil and/or gas wells are drilled by circulating in the borehole being drilled any of the fluids 1–38 set forth in tables 2–6 and 8 while drilling utilizing a rotary drilling process, the fluids containing sufficient weight material to provide the fluids with sufficient density to withstand the formation pressures encountered in the subterranean formations drilled.

TABLE 1

15 pbw Chitosan, 7.5 pbw Succinic Anhydride

| SAMC Sample Number | Initial Water pbw | Methanol pbw | Additional Water pbw | Other Modifier (OM) | OM pbw |
|---|---|---|---|---|---|
| 1 | 9 | 0 | 9 | None | 0 |
| 2 | 9 | 7.1 | 0 | None | 0 |
| 3 | 9 | 3.86 | 0 | None | 0 |
| 4 | 9 | 5.45 | 0 | None | 0 |
| 5 | 9 | 8.66 | 0 | None | 0 |
| 6 | 9 | 10.19 | 0 | None | 0 |
| 7 | 9 | 11.63 | 0 | None | 0 |
| 8 | 7 | 7.1 | 0 | None | 0 |
| 9 | 8 | 7.1 | 0 | None | 0 |
| 10 | 9 | 7.1 | 0 | None | 0 |
| 11 | 10 | 7.1 | 0 | None | 0 |
| 12 | 11 | 7.1 | 0 | None | 0 |
| 13 | 12 | 7.1 | 0 | None | 0 |
| 14 | 9 | 0 | 0 | Polyglycerine ™ (Dow) | 11.51 |
| 15 | 9 | 0 | 0 | Jeffamine ED-600 (Texaco) | 9.42 |
| 16 | 9 | 0 | 0 | Jeffamine T-403 (Texaco) | 8.63 |
| 17 | 9 | 0 | 0 | Propyleneglycol Propyl Ether | 7.94 |
| 18 | 9 | 0 | 0 | Polyglycol P-425 (Dow) | 8.94 |
| 19 | 9 | 0 | 0 | Jeffamine ED-900 (Texaco) | 8.94 |

TABLE 2

All Fluids Contain 5 ppb Soda Ash in Tap Water

| Fluid | C-1 | 1 | 2 | 3 | 4 |
|---|---|---|---|---|---|
| SAMC #1, ppb | 11 | 11 | 11 | 11 | 11 |
| Methanol, ppb | 0 | 3.94 | 7.89 | 11.83 | 15.78 |
| Initial Properties | | | | | |
| Brookfield Viscosity | | | | | |
| 0.3 rpm, cp ($\times 10^{-3}$) | 27.4 | 36.7 | 56.8 | 91.3 | 145. |
| 0.5 rpm, cp ($\times 10^{-3}$) | 15.9 | 25.5 | 36.2 | 76.8 | 94.8 |
| 100 rpm, cp | 1206 | 1356 | 1452 | 1650 | 1884 |
| Temperature, °F. | 72.8 | 72.6 | 73.0 | 73.4 | 74.2 |
| Fann Rheology | | | | | |
| Plastic Viscosity | 49 | 49 | 45 | 52 | 51 |
| Yield Point | 83 | 87 | 93 | 88 | 83 |
| After Hot Rolling | | | | | |
| Brookfield Viscosity | | | | | |
| 0.3 rpm, cp ($\times 10^{-3}$) | 5.7 | 117 | 132. | 177. | 187. |
| 0.5 rpm, cp ($\times 10^{-3}$) | 6.9 | 67.4 | 77.5 | 117. | 127. |
| 100 rpm, cp | 714 | 1068 | 1272 | 1860 | 2040 |
| Temperature, °F. | 78.4 | 75.0 | 71.9 | 70.8 | 71.0 |
| Fann Rheology | | | | | |
| Plastic Viscosity | 39 | 39 | 40 | 42 | 28 |
| Yield Point | 35 | 61 | 64 | 78 | 106 |

TABLE 3

All Fluids Contain 5 ppb Soda Ash in Tap Water

| Fluid | 5 | 6 | 7 | 8 |
|---|---|---|---|---|
| SAMC #2, ppb | 11.6 | 11.6 | 11.6 | 11.6 |
| Blue Streak, ppb | 0 | 0.5 | 1.0 | 3.5 |
| Initial Properties | | | | |
| Density, ppg | 7.8 | 6.8 | 6.7 | 6.1 |
| Brookfield Viscosity | | | | |
| 0.3 rpm, cp ($\times 10^{-3}$) | 63.2 | 115. | 114. | 92.8 |
| 0.5 rpm, cp ($\times 10^{-3}$) | 40.4 | 70.0 | 72.9 | 67.4 |
| 100 rpm, cp | 2639 | 3419 | 3599 | 4379 |
| Temperature, °F. | 72.5 | 73.4 | 73.3 | 73.0 |
| Fann Rheology | | | | |
| Plastic Viscosity | 73 | 186 | ND | ND |
| Yield Point | 144 | 186 | ND | ND |
| After Hot Rolling | | | | |
| Density, ppg | 7.6 | 6.4 | 6.0 | 5.1 |
| PH | 9.50 | 9.55 | 9.55 | 9.55 |
| Brookfield Viscosity | | | | |
| 0.3 rpm, cp ($\times 10^{-3}$) | 181. | 218. | 256 | 235. |
| 0.5 rpm, cp ($\times 10^{-3}$) | 123. | 142. | 156. | 152. |
| 100 rpm, cp | 1722 | 3017 | 3437 | 5123 |
| Temperature, °F. | 78.4 | 80.9 | 74.7 | 75.9 |
| Fann Rheology | | | | |
| Plastic Viscosity | 56 | 51 | 61 | ND |
| Yield Point | 87 | 122 | 143 | ND |

TABLE 4

All Fluids Contain
5 ppb Soda Ash and 1 ppb BLUE STREAK in Tap Water

| Fluid | 9 | 10 | 11 | 12 | 13 | 14 |
|---|---|---|---|---|---|---|
| SAMC #/, ppb | 3/8.61 | 4/8.99 | 2/9.41 | 5/9.84 | 6/10.26 | 7/10.59 |
| | | | Initial Properties | | | |
| Density, ppb | 6.3 | 6.2 | 6.0 | 5.8 | 6.4 | 5.6 |
| Brookfield Viscosity | | | | | | |
| 0.3 rpm, cp ($\times 10^{-3}$) | 40.0 | 83.6 | 55.2 | 68.8 | 68.0 | 18.2 |
| 0.5 rpm, cp ($\times 10^{-3}$) | 29.3 | 56.4 | 39.6 | 53.7 | 50.6 | 13.6 |
| 100 rpm, cp | 1872 | 2417 | 2417 | 2555 | 2471 | 1806 |
| Temperature, °F. | 81.6 | 80.5 | 79.6 | 79.6 | 78.9 | 77.7 |
| Fann Rheology | | | | | | |
| Plastic Viscosity | 38 | 56 | 49 | 53 | 49 | 52 |
| Yield Point | 104 | 118 | 125 | 130 | 122 | 94 |
| | | | After Hot Rolling | | | |
| Density, ppg | 6.5 | 5.35 | 5.5 | 5.6 | 5.4 | 5.1 |
| pH | 9.9 | 9.9 | 9.9 | 10.0 | 10.0 | 10.0 |
| Brookfield Viscosity | | | | | | |
| 0.3 rpm, cp ($\times 10^{-3}$) | 99.6 | 116. | 112. | 148. | 145. | 121 |
| 0.5 rpm, cp ($\times 10^{-3}$) | 72.0 | 75.6 | 68.9 | 95.3 | 87.3 | 75.6 |
| 100 rpm, cp | 1512 | 1746 | 1518 | 2058 | 1824 | 1920 |
| Temperature, °F. | 80.1 | 76.7 | 75.9 | 77.0 | 77.4 | 77.5 |
| Fann Rheology | | | | | | |
| Plastic Viscosity | 42 | 35 | 45 | 50 | 52 | 49 |
| Yield Point | 79 | 107 | 102 | 98 | 106 | 89 |

TABLE 5

All Fluids Contain
5 ppb Soda Ash and 1 ppb BLUE STREAK in Tap Water

| Fluid | 15 | 16 | 17 | 18 | 19 | 20 |
|---|---|---|---|---|---|---|
| SAMC #/, ppb | 8/9.05 | 9/9.28 | 10/10.03 | 11/10.53 | 12/10.67 | 13/11.06 |
| | | | Initial Properties | | | |
| Density, ppb | 5.6 | 5.5 | 5.7 | 6.2 | 5.6 | 5.4 |
| Brookfield Viscosity | | | | | | |
| 0.3 rpm, cp ($\times 10^{-3}$) | 10.3 | 19.6 | 112. | 137. | 160. | 148. |
| 0.5 rpm, cp ($\times 10^{-3}$) | 10.6 | 16.5 | 76.0 | 110. | 104. | 108. |
| 100 rpm, cp | 2717 | 2603 | 3017 | 3779 | 3227 | 3767 |
| Temperature, °F. | 79.9 | 79.9 | 79.8 | 79.9 | 79.9 | 79.7 |
| Fann Rheology | | | | | | |
| Plastic Viscosity | 46 | 48 | 45 | 44 | 53 | 46 |
| Yield Point | 90 | 78 | 130 | 154 | 112 | 133 |
| | | | After Hot Rolling | | | |
| Density, ppg | 5.3 | 5.1 | 5.5 | 5.7 | 5.2 | 5.3 |
| pH | 9.8 | 9.8 | 9.8 | 9.7 | 9.8 | 9.8 |
| Brookfield Viscosity | | | | | | |
| 0.3 rpm, cp ($\times 10^{-3}$) | 120. | 110. | 146. | 176. | 152. | 130. |
| 0.5 rpm, cp ($\times 10^{-3}$) | 84.2 | 77.0 | 97.7 | 113. | 103. | 89.5 |
| 100 rpm, cp | 2513 | 2310 | 2555 | 2669 | 2591 | 2489 |
| Temperature, °F. | 80.3 | 80.1 | 80.6 | 80.5 | 80.9 | 80.8 |
| Fann Rheology | | | | | | |
| Plastic Viscosity | 41 | 43 | 45 | 54 | 44 | 46 |
| Yield Point | 89 | 86 | 96 | 107 | 98 | 97 |

TABLE 6

All Fluids Contain
5 ppb Soda Ash and 1 ppb BLUE STREAK in Tap Water

| Fluid | 21 | 22 | 23 | 24 | 25 | 26 |
|---|---|---|---|---|---|---|
| SAMC #/, ppb | 14/10.34 | 15/10.96 | 16/10.73 | 17/9.71 | 18/9.49 | 19/10.54 |
| | | | Initial Properties | | | |
| Density, ppb | 6.0 | 6.0 | 5.8 | 5.2 | 5.3 | 6.0 |
| Brookfield Viscosity | | | | | | |
| 0.3 rpm, cp ($\times 10^{-3}$) | 18.2 | 12.4 | 14.1 | 9.8 | 4.1 | 5.1 |
| 0.5 rpm, cp ($\times 10^{-3}$) | 15.9 | 12.3 | 13.0 | 4.6 | 4.6 | 5.7 |
| 100 rpm, cp | 1890 | 2052 | 2310 | 1620 | 1776 | 2220 |
| Temperature, °F. | 76.4 | 77.6 | 76.7 | 79.6 | 79.6 | 79.3 |
| Fann Rheology | | | | | | |
| Plastic Viscosity | 48 | 49 | 45 | 57 | 54 | 43 |
| Yield Point | 84 | 80 | 95 | 111 | 81 | 86 |
| | | | After Hot Rolling | | | |
| Density, ppg | 4.9 | 4.2 | 4.1 | 3.9 | 3.7 | 5.3 |
| pH | 10.0 | 10.0 | 10.0 | 9.9 | 9.9 | 9.9 |
| Brookfield Viscosity | | | | | | |
| 0.3 rpm, cp ($\times 10^{-3}$) | 105. | 72.0 | 33.7 | 104. | 99.2 | 91.2 |
| 0.5 rpm, cp ($\times 10^{-3}$) | 76.8 | 54.5 | 24.7 | 63.1 | 61.4 | 74.4 |
| 100 rpm, cp | 2064 | 1770 | 1854 | 2651 | 2345 | 2459 |
| Temperature, °F. | 79.7 | 79.6 | 76.2 | 78.9 | 79.8 | 78.5 |
| Fann Rheology | | | | | | |
| Plastic Viscosity | 43 | 44 | 39 | 52 | 43 | 47 |
| Yield Point | 83 | 80 | 76 | 87 | 89 | 89 |

TABLE 7

Polar Additive Designations in Table 8

| Polar Additive # in Table 8 | Polar Additive |
|---|---|
| 1 | Tetraethylenepentamine |
| 2 | Diethanolamine |
| 3 | JEFFAMINE ED-600 |
| 4 | Ethanol |
| 5 | Methanol |
| 6 | JEFFAMINE ED-2001 |
| 7 | POLYGLYCERINE |
| 8 | Polyethyleneglycol 200 |
| 9 | Isopropanol |
| 10 | Hexylene glycol |
| 11 | Glycerine |
| 12 | Polyethyleneglycol 8000 |

TABLE 8

All Fluids Contain 8.6 ppb SAMC #1 and 5 ppb Soda Ash

| Fluid | C-2 | 27 | 28 | 29 | 30 | 31 | 32 | 33 | 34 |
|---|---|---|---|---|---|---|---|---|---|
| Polar Additive (PA) | None | 1 | 2 | 3 | 4 | 5 | 6 | 7 | 8 |
| PA, ppb | 0 | 10 | 10 | 10 | 10 | 10 | 10 | 10 | 10 |
| Initial Properties |
| pH | 9.77 | 10.60 | 10.19 | 10.07 | 9.78 | 9.78 | 9.91 | 9.80 | 9.72 |
| 0.3 rpm, cp ($\times 10^{-3}$) | 62.8 | 206 | 95.6 | 144 | 83.9 | 129 | 118 | 95.2 | 58.8 |
| 0.5 rpm, cp ($\times 10^{-3}$) | 1544 | 2939 | 1710 | 2118 | 1824 | 1980 | 2154 | 1788 | 1890 |
| PV, cp | 40 | 46 | 41 | 44 | 47 | 44 | 45 | 42 | 45 |
| YP, lb/100 sq. ft. | 104 | 87 | 80 | 95 | 96 | 91 | 98 | 93 | 90 |
| Hot Rolled at 180° F. for 16 Hours |
| 0.3 rpm, cp ($\times 10^{-3}$) | 38.7 | 220 | 192 | 202 | 178 | 176 | 197 | 153 | 89.6 |
| 0.5 rpm, cp ($\times 10^{-3}$) | 885 | 3029 | 2843 | 2735 | 1992 | 1942 | 2310 | 1812 | 1410 |
| PV, cp | 40 | 44 | 43 | 43 | 40 | 41 | 45 | 45 | 37 |
| YP, lb/100 sq. ft. | 47 | 97 | 86 | 87 | 75 | 69 | 85 | 58 | 45 |
| Hot Rolled at 250° F. for 16 Hours |
| pH | 9.54 | 11.01 | 10.24 | 10.04 | 9.51 | 8.14 | 9.75 | 9.66 | 9.53 |
| 0.3 rpm, cp ($\times 10^{-3}$) | 0.64 | 140 | 131 | 71.2 | 38.6 | 33.3 | 5.3 | 2.9 | 0.92 |
| 100 rpm, cp | 98 | 1710 | 1518 | 1392 | 996 | 691 | 384 | 178 | 209 |
| PV, cp | 20 | 42 | 41 | 44 | 37 | 32 | 29 | 25 | 40 |
| YP, lb/100 sq. ft. | 10 | 76 | 72 | 51 | 37 | 38 | 25 | 23 | 7 |

| Fluid | 35 | 36 | 37 | 38 |
|---|---|---|---|---|
| Polar Additive (PA) | 9 | 10 | 11 | 12 |
| PA, ppb | 10 | 10 | 10 | 10 |
| Initial Properties |
| pH | 9.74 | 9.68 | 9.63 | 9.72 |
| 0.3 rpm, cp ($\times 10^{-3}$) | 62.4 | 119 | 42.8 | 98.9 |
| 100 rpm, cp ($\times 10^{-3}$) | 1590 | 1932 | 1134 | 2142 |
| PV, cp | 45 | 46 | 47 | 49 |
| YP, lb/100 sq. ft. | 84 | 104 | 69 | 98 |
| Hot Rolled at 180° F. for 16 Hours |
| 0.3 rpm, cp ($\times 10^{-3}$) | 159 | 21 | 78.8 | 125 |
| 100 rpm, cp | 1572 | 984 | 1158 | 1626 |
| PV, cp | 41 | 34 | 42 | 40 |
| YP, lb/100 sq. ft. | 70 | 30 | 51 | 67 |
| Hot Rolled at 250° F. for 16 Hours |
| pH | 9.60 | 9.55 | 9.48 | 9.52 |
| 0.3 rpm, cp ($\times 10^{-3}$) | 0.30 | 0.24 | 0.14 | 0.04 |
| 100 rpm, cp | 17 | 29 | 113 | 12 |
| PV, cp | 25 | 18 | 26 | 30 |
| YP, lb/100 sq. ft. | 14 | 5 | 19 | 4 |

The data in Table 2 indicate the enhanced LSRV obtained by adding the Polar Additive methanol to the succinic anhydride-modified chitosan containing fluids. The data in Table 3 indicate the effect of the surfactant on decreasing the density and increasing the viscosity of the fluids containing the succinic anhydride and methanol-modified chitosan. The data in Table 4 indicate the effect of the concentration of methanol in the succinic anhydride and methanol-modified chitosan on the viscosity of fluids prepared therefrom. The data in Table 5 indicate the effect of the concentration of water in the succinic anhydride and methanol-modified chitosan on the viscosity of fluids prepared therefrom. The data in Table 6 indicate the effect of various Polar Additives on the viscosity of alkaline fluids prepared therefrom The data in Table 8 indicate the enhanced LSRV obtained by adding various Polar Additives to the succinic anhydride-modified chitosan-containing fluids, particularly after aging the fluids at 180° F. Noteworthy also is the enhanced thermal stability on aging the fluids at 250° F. containing the Polar Additives tetraethylenepentamine, diethanolamine, JEFFAMINE ED-600, ethanol, and methanol.

What is claimed is:

1. A method of drilling a well wherein a drilling fluid is circulated in the wellbore during drilling comprising circulating as the drilling fluid an aqueous alkaline, chitosan-containing fluid which additionally contains an anhydride modifier and a polar additive comprising water soluble compounds containing one or more hydroxyl groups or one or more amino groups, including compounds containing both hydroxyl and amino groups, wherein the polar additive has a molecular weight less than about 2000.

2. The method of claim 1 wherein the anhydride is selected from the group consisting of alkanedioic acid anhydrides, alkenedioic acid anhydrides, substituted products of such anhydrides, and mixtures thereof, wherein the substituted products contain one or more functional groups selected from the group consisting of hydroxyl, carboxyl, alkenyl, amino, and mixtures thereof.

3. The method of claim 1 wherein the anhydride is selected from the group consisting of succinic anhydride, maleic anhydride, alkenylsuccinnic anhydrides wherein the alkenyl group contains from about 2 to about 20 carbon atoms, and mixtures thereof.

4. The method of claim 1 wherein the anhydride is dodecenylsuccinic anhydride.

5. The method of claim 1 wherein the anhydride is succinic anhydride.

6. The method of claim 5 wherein the weight ratio of anhydride to chitosan is from about 0.1 to 1 to about 1.5 to 1.

7. The method of claim 1, 2, 3, or 4 wherein the weight ratio of anhydride to chitosan is from about 0.1 to 1 to about 2.5 to 1.

8. The method of claim 1, 2, 3, 4, 5, or 6 wherein the fluid additionally contains an aldehyde therein.

9. The method of claim 8 wherein the aldehyde is selected from the group consisting of aldose or ketose sugars, oligosaccharides of the sugars containing up to about 10 sugar groups per molecule, alkanals containing from 1 to about 20 carbon atoms, substituted alkanals containing one or more functional groups, benzaldehyde, substituted benzaldehydes wherein the benzene ring contains one or more functional groups, and mixtures thereof.

10. The method of claim 1, 2, 3, 4, 5, or 6 wherein the polar additive is selected from the group consisting of monoalcohols, polyalcohols, glycolethers, polyalkyleneglycols, polyglycerols, monoamines, polyamines, amino-substituted aliphatic alcohols, ethoxylated amines, and mixtures thereof.

11. The method of claim 1, 2, 3, 4, 5, or 6 wherein the polar additive is selected from the group consisting of (a) monoalcohols containing from one to about six carbon atoms, (b) polyalcohols having at least two carbon atoms and two hydroxyl groups but no more than 18 carbon atoms and 31 hydroxyl groups, (c) glycol ethers, (d) polyalkyleneglycols, (e) monoamines containing from one to about six carbon atoms, (f) polyamines, (g) amino-substituted aliphatic alcohols, (h) ethoxylated amines, and mixtures thereof.

12. A well drilling and servicing fluid comprising an alkaline aqueous liquid, chitosan, an alkanedioic acid anhydride, and a polar additive comprising water soluble compounds containing one or more amino groups, including compounds containing both hydroxyl and amino groups, wherein the polar additive has a molecular weight less than about 2000.

13. The fluid of claim 12 wherein the anhydride is selected from the group consisting of alkanedioic acid anhydrides, substituted products of such anhydrides, and mixtures thereof, wherein the substituted products contain one or more functional groups selected from the group consisting of hydroxyl, carboxyl, alkenyl, amino, and mixtures thereof.

14. The fluid of claim 12 wherein the anhydride is selected from the group consisting of succinic anhydride, alkenylsuccinnic anhydrides wherein the alkenyl group contains from about 2 to about 20 carbon atoms, and mixtures thereof.

15. The fluid of claim 12 wherein the anhydride is dodecenylsuccinic anhydride.

16. The fluid of claim 12 wherein the anhydride is succinic anhydride.

17. The fluid of claim 16, wherein the weight ratio of anhydride to chitosan is from about 0.1 to 1 to about 1.5 to 1.

18. The fluid of claim 12, 13, 14, or 15 wherein the weight ratio of anhydride to chitosan is from about 0.1 to 1 to about 2.5 to 1.

19. The fluid of claim 12, 13, 14, 15, 16, or 17 wherein the fluid additionally contains an aldehyde therein.

20. The fluid of claim 19 wherein the aldehyde is selected from the group consisting of aldose or ketose sugars, oligosaccharides of the sugars containing up to about 10 sugar groups per molecule, alkanals containing from 1 to about 20 carbon atoms, substituted alkanals containing one or more functional groups, benzaldehyde, substituted benzaldehydes wherein the benzene ring contains one or more functional groups, and mixtures thereof.

21. The fluid of claim 12, 13, 14, 15, 16, or 17 wherein the polar additive is selected from the group consisting of monoamines, polyamines, amino-substituted aliphatic alcohols, ethoxylated amines, and mixtures thereof.

22. The fluid of claim 12, 13, 14, 15, 16, or 17 wherein the polar additive is selected from the group consisting of (a) monoamines containing from one to about six carbon atoms, (b) polyamines, (c) amino-substituted aliphatic alcohols, (d) ethoxylated amines, (e) and mixtures thereof.

23. An anhydride-modified chitosan-containing composition comprising chitosan, an alkanedioic acid anhydride, a polar additive, and water, wherein the polar additive comprises water soluble compounds containing one or more amino groups, including compounds containing both hydroxyl and amino groups, wherein the polar additive has a molecular weight less than about 2000.

24. The anhydride-modified chitosan containing composition of claim 23 wherein the anhydride is selected from the group consisting of alkanedioic acid anhydrides, substituted products of such anhydrides, and mixtures thereof, wherein the substituted products contain one or more functional groups selected from the group consisting of hydroxyl, carboxyl, alkenyl, amino, and mixtures thereof.

25. The anhydride-modified chitosan containing composition of claim 23 wherein the anhydride is selected from the group consisting of succinic anhydride, alkenylsuccinnic anhydrides wherein the alkenyl group contains from about 2 to about 20 carbon atoms, and mixtures thereof.

26. The anhydride-modified chitosan containing composition of claim 23 wherein the anhydride is succinic anhydride.

27. The anhydride-modified chitosan containing composition of claim 23, 24, 25, or 26 wherein the weight ratio of anhydride to chitosan is from about 0.1 to 1 to about 1.5 to b 1.

28. The anhydride-modified chitosan containing composition of claim 23, 24, 25, or 26 wherein the polar additive is selected from the group consisting of monoamines, polyamines, amino-substituted aliphatic alcohols, ethoxylated amines, and mixtures thereof.

29. The anhydride-modified chitosan containing composition of claim 23, 24, 25, or 26 wherein the polar additive is selected from the group consisting of (a) monoamines containing from one to about six carbon atoms, (b) polyamines, (c) amino-substituted aliphatic alcohols, (d) ethoxylated amines, and (e) mixtures thereof.

30. The method of preparing a modified chitosan comprising mixing under high shear conditions chitosan, an organic diacid anhydride, water, and a polar additive wherein the concentration of the chitosan is from 20% to 60% by weight, the concentration of the anhydride is from 5% to 45% by weight, the concentration of water is from 10% to 30% by weight, and the concentration of the polar additive is from 10% to 25% by weight, and wherein the polar additive comprises water soluble compounds containing one or more hydroxyl groups or one or more amino groups, including compounds containing both hydroxyl and amino groups, wherein the polar additive has a molecular weight less than about 2000.

31. The method of claim 30 wherein the anhydride is selected from the group consisting of alkanedioic acid anhydrides, alkenedioic acid anhydrides, substituted products of such anhydrides, and mixtures thereof, wherein the substituted products contain one or more functional groups selected from the group consisting of hydroxyl, carboxyl, alkenyl, amino, and mixtures thereof.

32. The method of claim 30 wherein the anhydride is selected from the group consisting of succinic anhydride, maleic anhydride, alkenylsuccinnic anhydrides wherein the alkenyl group contains from about 2 to about 20 carbon atoms, and mixtures thereof.

33. The method of claim 30 wherein the anhydride is succinic anhydride.

34. The method of claim 20, 31, 32, or 33 wherein the weight ratio of anhydride to chitosan is from about 0.1 to 1 to about 1.5 to 1.

35. The method of claim 30, 31, 32, or 33 wherein the polar additive is selected from the group consisting of monoalcohols, polyalcohols, glycolethers, polyalkyleneglycols, polyglycerols, monoamines, polyamines, amino-substituted aliphatic alcohols, ethoxylated amines, and mixtures thereof.

36. The method of claim 30, 31, 32, or 33 wherein the polar additive is selected from the group consisting of (a) monoalcohols containing from one to about six carbon atoms, (b) polyalcohols having at least two carbon atoms and two hydroxyl groups but no more than 18 carbon atoms and 31 hydroxyl groups, (c) glycol ethers, (d) polyalkyleneglycols, (e) monoamines containing from one to about six carbon atoms, (f) polyamines, (g) amino-substituted aliphatic alcohols, (h) ethoxylated amines, and mixtures thereof.

37. The method of claim 1, 3, 5, or 6 wherein the polar additive is selected from the group consisting of polyethyleneamines-containing up to about 20 carbon atoms, ethanolamines, monoalcohols containing up to about six carbon atoms, glycol ethers containing one free hydroxyl group, and mixtures thereof.

38. The fluid of claim 12, 14, 16, or 17 wherein the polar additive is selected from the group consisting of polyethyleneamines-containing up to about 20 carbon atoms, ethanolamines, and mixtures thereof.

39. The anhydride-modified chitosan-containing composition of claim 23, 25, or 27 wherein the polar additive is selected from the group consisting of polyethyleneamines-containing up to about 20 carbon atoms, ethanolamines, and mixtures thereof.

* * * * *